United States Patent [19]
Bogentoft

[11] 4,191,744
[45] Mar. 4, 1980

[54] NEUTRALIZING AGENT

[75] Inventor: Conny B. Bogentoft, Mölndal, Sweden

[73] Assignee: Aktiebolaget Hassle, Mölndal, Sweden

[21] Appl. No.: 856,912

[22] Filed: Dec. 2, 1977

Related U.S. Application Data

[63] Continuation of Ser. No. 802,416, Jun. 1, 1977, abandoned.

[51] Int. Cl.$^{2}$ .............................................. A61K 31/74
[52] U.S. Cl. ...................................................... 424/78
[58] Field of Search .......................................... 424/78

[56] References Cited

U.S. PATENT DOCUMENTS 3,224,940 12/1965 Ainsworth et al. .................... 424/78
3,326,755 6/1967 Sheth .................................... 424/157
3,332,841 7/1967 Ainsworth et al. .................... 424/78

*Primary Examiner*—Frederick E. Waddell
*Attorney, Agent, or Firm*—Brumbaugh, Graves, Donohue & Raymond

[57] ABSTRACT

A gastric acid neutralizing agent in the form of a clear aqueous solution of a watersoluble, non-crosslinked polyethyleneimine, a taste improving acid selected from the group of alginic acid, polygalacturonic acid, galacturonic acid, pectin, tannic acid, arabic acid, galactaric acid and glutaric acid and an organic acid selected from the group of tartaric acid, fumaric acid, phosphoric acid, acetic acid, citric acid, succinic acid, and malic acid, the latter acid in such an amount that the pH of the solution is 4 to 11; a process for preparing such gastric acid neutralizing agent and a method for treatment of hyperacidity comprising oral administration of such agent.

16 Claims, No Drawings

NEUTRALIZING AGENT

This application is a continuation in part of my application Ser. No. 802,416 filed June 1, 1977, now abandoned.

The present invention relates to a gastric acid neutralizing agent in the form of a solution, a process for its preparation, and a method for neutralizing gastric acid in mammals, including man.

The object of the present invention is to obtain a gastric acid neutralizing solution which gives a fast reaction with an acid, has a high acid neutralizing capacity, is not absorbed and does not give pharmacological systemic effects, is well tolerated and is welltasting and has a good consistency.

An antacid ought to have i.a. high reaction speed with diluted acid and a high acidbinding capacity. Hitherto known antacid preparations, which fulfills this requirement to the very best contain aluminum hyroxide or related compounds, alone or in combination with magnesium salts. Aluminum hydroxide and related compounds have the advantage of reacting relatively fast with acids at a lower pH. The reaction stops, however, when the pH-value rises to about 4. Other compounds having been used to a relatively high extent as an antacid is magnesium silicate and calcium carbonate. These two compounds buffer at a somewhat higher pH-value than the aluminum and they are partly resorbed. Other magnesium compounds, as the hydroxide and the carbonate, are only used to a limited extent as such. They are however, often combined with aluminum hydroxide due to the fact that the compounds themselves give a strong laxative effect, which is neutralized by the combination with aluminum hydroxide. Sodium bicarbonate is a completely watersoluble compound which has been used to a certain extent as antacid, as well. This compound, however, raises the pH-value to above the neutral point, which may stimulate an increased secretion of gastric acid. Furthermore it is completely resorbed and may create alkalose.

Most of the antacid active compounds hitherto used are thus compounds which are difficult to dissolve in water, but which dissolve in gastric juice while reacting with hydrochloric acid. The reaction is not momentaneous, as the reaction between an acid and a base in as solution. At the reaction between a solid and a liquid phase, which is the case hereby, the reaction speed depends on i.a. the particle size (or more correct the contact surface between the phases), the solubility of the solid phase, the crystal structure, possible hydralation etc. It is a wellknown clinical observation that a liquid preparation of e.g. aluminum hydroxide gives better effect than tablets (e.g. Krantz and Carr, Pharmacol. Principles Med. Practic. Williams and Wilkins, Baltimore 1961, page 391). One of the most important reasons for this being the case is that the liquid preparations react faster with acid than do tablets (Sjögren, Farm.Revy. 62, 735, 1963).

These hitherto known and used antacids containing a combination of Al- and Mg-salts do, however, show certain drawbacks as bad taste and chalky consistency, and a relatively slow reactivity with acid. Another drawback using this type of antacids is that an increase of the pH of the urine may occur, which leads to a faster secretion of acidic therapeutic agents which may be administered simultaneously. Interaction with other drugs such as anticholinergic agents and tetracyclines in the gastrointestinal tract may occur as well, so that the latter are resorbed to a less degree than intended.

To obtain a liquid preparation the Al- and Mg-salts must be suspended in water. Such suspensions have proved to be unappetizing to many patients due to their unpleasant consistency, their colour and lack of transparancy.

U.S. Pat. No. 3,224,940 discloses the use of polyalkylenimines, which are cross-linked by means of a cross-linking agent such as butadiene-dioxide, in combination with a conventional antacid such as the Al- or Mg-salts mentioned above in antacid preparation. This patent also touches upon the use of non-crosslinked polyethyleneimines in combination with the conventional antacids in antacid preparations.

U.S. Pat. No. 3,332,841 discloses the use of water-insoluble polyalkyleneimines crosslinked by means of a crosslinking agent. The patent is related solely to such crosslinked polyalkyleneimines which may be used without other antacids.

However the prior art does not provide or suggest how to obtain a liquid antacid preparation in the form of a clear antacid solution.

It has now surprisingly been found possible to overcome above drawbacks by means of the present invention which provides a liquid gastric acid neutralizing preparation in the form of a clear solution comprising an aqueous solution of a substantial amount of a water-soluble, substantially non-crosslinked polyethylene-imine, at least one taste improving acid selected from the group consisting of alginic acid, polygalacturonic acid, galacturonic acid, pectin, tannic acid, arabic acid, galactaric acid, and glutaric acid, and at least one acid selected from the group consisting of tartaric acid, fumaric acid, phosphoric acid, acetic acid, citric acid, succinic acid, and malic acid, the acid(s) from the latter group in such an amount that the pH of the preparation is 4 to 11, the preparation being substantially free from water-insoluble antacid compounds.

By water-soluble is meant that water containing an amount up to at least 60% by weight of the polyethyleneimine is clear and free from precipitate.

By a "non-crosslinked polyethyleneimine" is meant a polyethyleneimine, which has not been subjected to reaction with a cross-linking agent, such as those agents suggested by the above-mentioned U.S. Patents.

The above definitions provide a preparation in the form of a clear solution, as desired. The gastric acid neutralizing preparation is prepared by a process, which is characterized in that an aqueous solution of a water-soluble, substantially non-crosslinked polyethylene-imine is added to at least one organic acid selected from the group consisting of alginic acid, polygalacturonic acid, galacturonic acid, pectin, tannic acid, arabic acid, galactaric acid, and glutaric acid, whereupon in order to change pH at least one organic acid selected from the group consisting of tartaric acid, fumaric acid, phosphoric acid, acetic acid, citric acid, succinic acid and malic acid is added, whereby said latter acid is added in such an amount that pH is 4 to 11.

According to a preferred embodiment the watersoluble substantially non-crosslinked polyethyleneimine has a molecular weight of 500 to 5000, and preferably, a viscosity of about 200 cps as a 50% aqueous solution.

According to a further preferred embodiment the liquid gastric acid neutralizing preparation contains up to 60% by weight of a polyethyleneimine when a solution intended to be diluted before use is prepared, whereby preferably the preparation contains 10 to 40% by weight of a polyethyleneimine when a solution intended for direct administration is prepared.

According to another aspect of the invention this relates to the process for preparing the liquid gastric acid neutralizing agent according to the above given definitions, including preferred embodiments, as well.

According to a further aspect of the invention this also relates to a method for treatment of hyperacidity and ulcer disease by administering an effective amount of a preparation according to the above given definitions including preferred embodiments.

The agent as prepared has the ability of neutralizing the acid of the gastric juice in the stomach to a desired pH without giving any unsuitable side effects.

The polyethyleneimines used, according to the present invention, are watersoluble polyethyleneimines of the formula

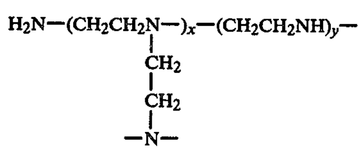

of which suitable qualities are sold under the marks G35 and G50 by BASF (Badische Anilin und Soda Fabriken) Federal Republic of Germany, and under the marks PEI 6, PEI 12 and PEI 18 by Dow Chemicals, USA.

In order to obtain a gastric acid neutralizing agent such polyethyleneimines, however must be provided with at least one organic acid for pH-decreasing purposes, whereby such an acid is selected from the group consisting of tartaric acid, fumaric acid, phosphoric acid, citric acid, acetic acid, succinic acid and malic acid, whereby the acid is preferably selected from the group citric acid, acetic acid, succinic acid, and malic acid.

In order to obtain and improve palatability the acid-polyalkyleneimine solution has further to be provided with at least one taste improving acid selected from the group consisting of alginic acid, polygalacturonic acid, galacturonic acid, pectin, tannic acid, arabic acid, galactaric acid and glutaric acid, whereby preferably alginic acid, polygalacturonic acid, galacturonic acid, and pectin are used. The amount of taste improving acid should be an effective amount for obtaining a palatable preparation, normally 1–10, preferably 1–5% of the weight of the preparation.

In order to get the best palatability a preferred embodiment of the invention comprises adding the polyethyleneimine as an aqueous solution to a solution of the taste improving acid, whereupon the pH-regulating acid is added until desired pH is reached.

The invention will be described more in detail below with reference to the Examples given, however, without being restricted thereto. "100%" below indicates that the weight of the polyethyleneimine is expressed as the weight of pure (100%) compound, although the compound is added as an aqueous solution.

| Example 1 | | |
|---|---|---|
| Polyethyleneimine 100% (G35, BASF) | | 250 g |
| Alginic acid | | 20 g |
| Citric acid | | 100 g |
| Water | ad | 1000 g |

The alginic acid was dissolved in 380 mls of water. Then the polyethyleneimine was added as a 50% aqueous solution. After careful stirring the pH value was adjusted to 7.3 by adding the citric acid. The resulting solution was a clear, light yellow solution.

| Example 2 | | |
|---|---|---|
| Polyethyleneimine 100% (G35, BASF) | | 250 g |
| Galacturonic acid | | 20 g |
| Acetic acid | | 160 g |
| Water | ad | 1000 g |

The galacturonic acid was dissolved in 320 mls of water, whereupon the polyethyleneimine was added as a 50% solution. After careful mixing the acetic acid was added, whereby a clear, faintly orange solution having a pH of 7.5 was obtained.

| Example 3 | | |
|---|---|---|
| Polyethyleneimine G35, 100% | | 240 g |
| Polygalacturonic acid | | 16 g |
| Phosphoric acid | | 200 g |
| Water | ad | 1000 g |

The preparation is prepared in accordance with Example 1 above, whereby final pH of 6.0 is obtained.

| Example 4 | | |
|---|---|---|
| Polyethyleneimine G35, 100% | | 210 g |
| Polygalacturonic acid | | 14 g |
| Phosphoric acid | | 205 g |
| Acetic acid | | 90 g |
| Water | ad | 1000 g |

The preparation was prepared in accordance with Example 1 above, whereby a final pH of 5.0 was obtained.

| Example 5 | | |
|---|---|---|
| Polyethyleneimine (100%) | | 250 g |
| Pectin | | 20 g |
| Acetic acid | | 150 g |
| Water | ad | 1000 g |

The preparation is obtained in accordance with Example 1 above. pH is about 7.

| Example 6 | | |
|---|---|---|
| Polyethyleneimine (100%) | | 230 g |
| Arabic acid | | 13 g |
| Phosphoric acid | | 230 g |
| Water | ad | 1000 g |

The preparation is obtained in accordance with Example 1 above. Final pH is 6.4.

| Example 7 | | |
|---|---|---|
| Polyethyleneimine (100%) | | 260 g |
| Tannic acid | | 17 g |

-continued

| Example 7 | | |
|---|---|---|
| Acetic acid | | 130 g |
| Water | ad | 1000 g |

The preparation is obtained in accordance with Example 1 above. Final pH is 7.6.

| Example 8 | | |
|---|---|---|
| Polyethyleneimine (100%) | | 250 g |
| Alginic acid | | 17 g |
| Succinic acid | | 170 g |
| Water | ad | 1000 g |

The preparation is obtained in accordance with Example 1 above. Final pH 7.1.

| Example 9 | | |
|---|---|---|
| Polyethyleneimine (100%) | | 250 g |
| Galactaric acid | | 17 g |
| Acetic acid | | 130 g |
| Water | ad | 1000 g |

The preparation is prepared in accordance with Example 1 above. Final pH is about 7.5.

| Example 10 | | |
|---|---|---|
| Polyethyleneimine (100%) | | 250 g |
| Glutaric acid | | 17 g |
| Acetic acid | | 130 g |
| Water | ad | 1000 g |

The preparation is prepared in accordance with Example 1 above. Final pH is about 7.5

| Example 11 | | |
|---|---|---|
| Polyethyleneimine (100%) | | 250 g |
| Alginic acid | | 20 g |
| Malic acid | | 170 g |
| Water | ad | 1000 g |

The preparation is prepared in accordance with Example 1 above. Final pH is about 7.3. Fumaric acid and tartaric acid may be used as well.

| Example 12 | | |
|---|---|---|
| Polyethyleneimine (100%) | | 250 g |
| Polygalacturonic acid | | 50 g |
| Alginic acid | | 25 g |
| Phosphoric acid | | 100 g |
| Water | ad | 1000 g |

The preparation was prepared by dissolving polygalacturonic acid and alginic acid in 325 mls of water. Polyethyleneimine was then added as a 50% aqueous solution. After thorough stirring phosphoric acid was added. Final pH 8.6.

| Example 13 | | |
|---|---|---|
| Polythyleneimine (100%) | | 250 g |
| Alginic acid | | 50 g |
| Arabic acid | | 25 g |
| Sucinic acid | | 80 g |
| Water | ad | 1000 g |

Alginic acid and arabic acid were dissolved in 345 mls of water. Polyethyleneimine was then added as a 50% aqueous solution. After thorough stirring succinic acid was added. Final pH 8.9.

| Example 14 | | |
|---|---|---|
| Polyethyleneimine (100%) | | 250 g |
| Alginic acid | | 30 g |
| Galactaric acid | | 30 g |
| Phosphoric acid | | 100 g |
| Water | ad | 1000 g |

The preparation was prepared in accordance with Examples 12–13 above. The final pH obtained was 8.6.

| Example 15 | | |
|---|---|---|
| Polyethyleneimine (100%) | | 250 g |
| Polygalacturonic acid | | 50 g |
| Alginic acid | | 25 g |
| Phosphoric acid | | 150 g |
| Water | ad | 1000 g |

The preparation was prepared by dissolving polygalacturonic acid and alginic acid in 325 mls of water. Polyethyleneimine was then added as a 50% aqueous solution. After thorough stirring phosphoric acid was added. Final pH 7.5.

| Example 16 | | |
|---|---|---|
| Polyethyleneimine (100%) | | 250 g |
| Alginic acid | | 50 g |
| Arabic acid | | 25 g |
| Succinic acid | | 140 g |
| Water | ad | 1000 g |

Alginic acid and arabic acid were dissolved in 345 mls of water. Polyethyleneimine was then added as a 50% aqueous solution. After thorough stirring succinic acid was added. Final pH 7.6.

| Example 17 | | |
|---|---|---|
| Polyethyleneimine (100%) | | 250 g |
| Alginic acid | | 30 g |
| Galactaric acid | | 30 g |
| Phosphoric acid | | 150 g |
| Water | ad | 1000 g |

The preparation was prepared in accordance with Examples 12–13 above. The final pH obtained was 7.6.

The acid neutralizing capacities of the preparations above are 40–50 mls of 0.1 N HCl/g of 25% aqueous solution of polyethyleneimine. The reaction is finished within 1–2 min.

The daily dose of a preparation according to the invention depends very much on the degree of hyperacidity the patient is suffering from. Normal cases, however, require an amount of 8 to 40 g/24 hrs of the preparation when the preparation contains 25% of the polyethyleneimine. Single doses are 2–4 g, which are administered 4 to 10 times/24 hrs. Specific weight of the preparations above is about 1.25 g/ml.

Additionally the preparations may contain i.a. flavouring agents, effervescing agents and other water-soluble additives known in the art.

I claim:

1. A liquid gastric acid neutralizing preparation in the form of a clear solution, consisting essentially of an aqueous solution of a substantial amount of a water-soluble, substantially non-crosslinked polyethyleneimine, at least one taste-improving acid selected from the group consisting of alginic acid, polygalacturonic acid, galacturonic acid, pectin, tannic acid, arabic acid, galactaric acid, and glutaric acid, and at least one acid selected from the group consisting of tartaric acid, fumaric acid, phosphoric acid, acetic acid, citric acid, succinic acid, and malic acid, the acid(s) from the latter group in such an amount that the pH of the preparation is 4 to 11, the preparation being substantially free from water-insoluble antacid compounds.

2. A gastric acid neutralizing preparation according to claim 1, characterized in that the water-soluble substantially non-crosslinked polyethyleneimine has a molecular weight of 500 to 5000.

3. A gastric acid neutralizing preparation according to claim 1, characterized in that the polyethyleneimine has a viscosity of about 200 cps as a 50% aqueous solution.

4. A gastric acid neutralizing preparation according to claim 1, characterized in that the concentration of polyethyleneimine in a preparation intended to be diluted prior to administration is up to 60% by weight.

5. A gastric acid neutralizing preparation according to claim 1, characterized in that the concentration of polyethyleneimine in a preparation intended for administration is 10 to 40% by weight.

6. A gastric acid neutralizing preparation according to claim 1, characterized in that the acid selected from the first group of acids is present in an amount of 1 to 10, preferably 1 to 5% by weight.

7. A method for treatment of hyperacidity in a mammal including man suffering from such condition comprising oral administration of an effective amount of a liquid gastric acid neutralizing preparation in the form of a clear solution, consisting essentially of an aqueous solution of a substantial amount of a water-soluble, substantially non-crosslinked polyethyleneimine, at least one taste-improving acid selected from the group consisting of alginic acid, polygalacturonic acid, galacturonic acid, pectin, tannic acid, arabic acid, galactaric acid, and glutaric acid, and at least one acid selected from the group consisting of tartaric acid, fumaric acid, phosphoric acid, acetic acid, citric acid, succinic acid, and malic acid, the acid(s) from the latter group in such an amount that the pH of the preparation is 4 to 11, the preparation being substantially free from water-soluble antacid compounds.

8. A method according to claim 7, characterized in that the preparation administered consists essentially of polyethyleneimine having a molecular weight of 500 to 5000.

9. A method according to claim 7, characterized in that the preparation administered consists essentially of a polyethyleneimine, which has a viscosity of about 200 cps as a 50% aqueous solution.

10. A method according to claim 7, characterized in that the preparation administered consists essentially of a polyethyleneimine in an amount of 10 to 40% by weight.

11. A process for the preparation of a clear aqueous solution of a gastric acid neutralizing preparation, characterized in that an aqueous solution of a water-soluble, substantially non-crosslinked polyethyleneimine is added to at least one organic acid selected from the group alginic acid, polygalacturonic acid, galacturonic acid, pectin, tannic acid, arabic acid, galactaric acid, and glutaric acid, whereupon in order to change pH at least one acid selected from the group consisting of tartaric acid, fumaric acid, phosphoric acid, acetic acid, citric acid, succinic acid, and malic acid is added in such an amount that pH of an aqueous solution is 4 to 11.

12. A process according to claim 11, characterized in that a polyethyleneimine having a molecular weight of 500 to 5000 is utilized.

13. A process according to claim 11 characterized in that a polyethyleneimine that gives a viscosity of about 200 cps as a 50% aqueous solution, is utilized.

14. A process according to claim 11, characterized in that the concentration of polyethyleneimine in a preparation intended to be diluted prior to administration is up to 60% by weight.

15. A process according to claim 11, characterized in that the concentration of polyethyleneimine in a preparation intended for administration is 10 to 40% by weight.

16. A process according to claim 11, characterized in that the acid selected from the first group of acids is added in an amount of 1 to 10, preferably 1 to 5% by weight of the final preparation.

* * * * *

UNITED STATES PATENT AND TRADEMARK OFFICE

CERTIFICATE OF CORRECTION

PATENT NO. : 4,191,744

DATED : March 4, 1980

INVENTOR(S) : Conny Börje Bogentoft

It is certified that error appears in the above-identified patent and that said Letters Patent are hereby corrected as shown below:

Col. 8, line 6, "water-soluble" should read --water-insoluble--.

Signed and Sealed this

*Twenty-fourth* Day of *June 1980*

[SEAL]

*Attest:*

SIDNEY A. DIAMOND

*Attesting Officer* *Commissioner of Patents and Trademarks*